United States Patent
Fröberg et al.

(10) Patent No.: US 7,194,311 B1
(45) Date of Patent: Mar. 20, 2007

(54) DEVICE, METHOD, AND USE AT A MEDICAL IMPLANT

(75) Inventors: Paul Fröberg, Bromma (SE); Per Jarl, Järfälla (SE); Susanne Nilsson, Huddinge (SE)

(73) Assignee: St. Jude Medical AB, Jarfalla (SE)

( * ) Notice: Subject to any disclaimer, the term of this patent is extended or adjusted under 35 U.S.C. 154(b) by 626 days.

(21) Appl. No.: 10/111,764

(22) PCT Filed: Sep. 25, 2000

(86) PCT No.: PCT/SE00/01851

§ 371 (c)(1), (2), (4) Date: Jul. 31, 2002

(87) PCT Pub. No.: WO01/30444

PCT Pub. Date: May 3, 2001

(30) Foreign Application Priority Data

Oct. 26, 1999 (SE) ...................................... 9903868

(51) Int. Cl.
*A61N 1/00* (2006.01)
(52) U.S. Cl. ....................................................... 607/37
(58) Field of Classification Search ............. 607/36–38
See application file for complete search history.

(56) References Cited

U.S. PATENT DOCUMENTS

| | | | | |
|---|---|---|---|---|
| 4,479,489 A | * | 10/1984 | Tucci ........................... | 607/37 |
| 4,932,409 A | | 6/1990 | Hirschberg | |
| 5,307,955 A | * | 5/1994 | Viegas ........................ | 222/107 |
| 5,476,485 A | * | 12/1995 | Weinberg et al. ............. | 607/28 |
| 5,509,928 A | * | 4/1996 | Acken ......................... | 607/37 |

\* cited by examiner

*Primary Examiner*—George Manuel
(74) *Attorney, Agent, or Firm*—Schiff Hardin LLP

(57) ABSTRACT

A sealing plug having a self-sealing access slit is provided in a medical implant. An insert is inserted into the self-sealing access slit to preserve the slit during storage.

11 Claims, 2 Drawing Sheets

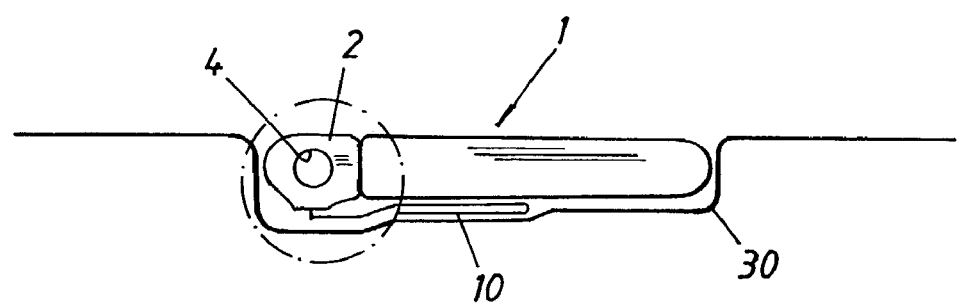
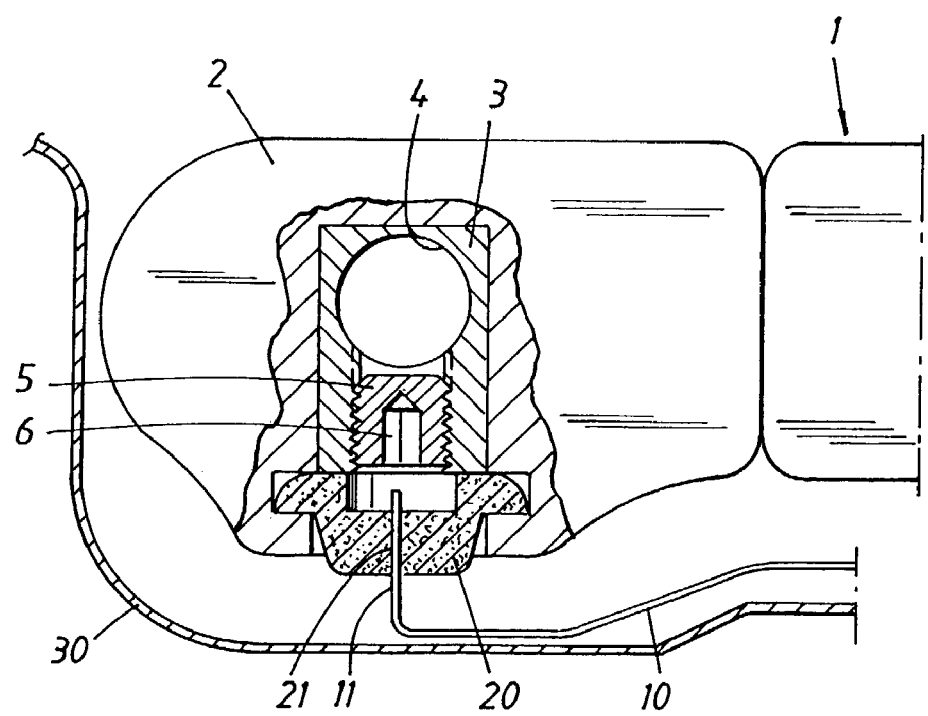

DEVICE, METHOD, AND USE AT A MEDICAL IMPLANT

BACKGROUND OF THE INVENTION

Technical Field of the Invention

The present invention relates generally to the field of medical implants. More specifically, the present invention relates to a sealing structure in a medical implant and a method of preserving the function during storage of self-sealing access slits in a sealing structure mounted in a medical implant.

Medical implants, heart stimulators, cardiac pacemakers, defibrillators, etc., are used for generating electric pulses, and for delivering these pulses to a heart. The pulses generated by a pulse generator within the implant are transmitted to the heart by at least one insulated electric conductor connected to the implant, which at the opposite end is provided with an electrode affixed to the conductor, generally an endocardial electrode. The conductor and the electrode are in a cardiac lead.

The endocardial electrode is in direct contact with the tissue within the heart, and may be anchored to the heart in order to prevent it from being dislodged due to the motion of the heart during heartbeats. Furthermore, the tissue of the heart grows around the electrode tip, which increases the fixation of the electrode to the tissue.

Medical implants run on batteries, which means that an implant must be replaced when its batteries are running low. To facilitate removal of the implanted pulse generator without having to remove the lead, medical implants are provided with a terminal block including a set or fixing screw for readily connecting and disconnecting an endocardial lead from the implant. Generally, such a fixing screw and terminal block are shielded from body fluids, while access to the fixing screw is allowed through the shield. The shielding protects the fixing screw and the terminal block from electric leakage and from the accumulation of solid body materials that could interfere with the manipulation of the fixing screw when disconnecting the lead from the implant.

U.S. Pat. No. 4,479,489, incorporated herein by reference, discloses such a shielding in the form of a mechanically self-sealing plug or structure for sealing the electrical terminal block of a cardiac pacing device from contact with body fluids while allowing access to a set screw of the terminal block when the plug is in place. The plug 28 is formed of an elastomeric material, inserted into a recess 24 of a medical implant, and secured within the recess with an adhesive material in addition to a compression fit. The plug includes a slit portion 30, cut out of the plug at the time of manufacturing, which allows for insertion of a tool into the slit for engagement with a set screw 20 of a terminal block 18. Upon removal of the tool, the slit 30 closes, thereby effectively sealing out body fluids from the set screw and the electrical terminal block.

When a medical implant is stored for a longer period prior to the implantation into a patient, the access slit(s) of a self-sealing structure, such as described in said U.S. patent, tends to net together. The opposite surfaces of the access slit sometimes are lubricated with a silicone-based lubricant, which further enhances the netting process.

SUMMARY OF THE INVENTION

It is an object of the present invention to provide for preservation of a self-sealing access slit in a sealing structure mounted in a medical implant.

In accordance with the present invention, in a sealing structure for a medical implant at least one self-sealing access slit is provided. An insert is provided in the access slit for minimizing a contact between opposite surfaces of the slit.

Further details and aspects of the invention will become apparent from the following detailed description of embodiments of the invention, reference being made to the accompanying drawings.

BRIEF DESCRIPTION OF THE DRAWINGS

FIG. 1 is a side elevational view of an insert according to one embodiment, in a medical implant with a storage tray, the insert being inserted into the medical implant.

FIG. 2 is an enlarged cross-sectional view of the insert, medical implant, and storage tray according to the embodiment shown in FIG. 1.

DETAILED DESCRIPTION OF PREFRRED EMBODIMENT

Figure 3A:
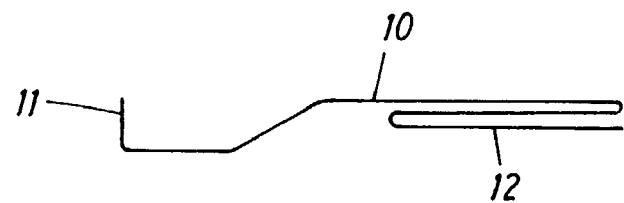
FIGS. 3a and 3b are side and top elevational views, respectively, of an insert according to an embodiment shown in a folded configuration.

For the purposes of promoting an understanding of the principles of the invention, reference will now be made to the preferred embodiment illustrated in the drawings and specific language will be used to describe the same. It will nevertheless be understood that no limitation of the scope of the invention is thereby intended, such alterations and further modifications in the illustrated device, and/or method, and such further applications of the principles of the invention as illustrated therein being contemplated as would normally occur now or in the future to one skilled in the art to which the invention relates.

Use is made of an insert for preserving a self-sealing slit during storage.

Preferably, use is made of an insert that at one end, the distal end, is provided with protrusions, e.g. in the shape of tongues or leaves, for insertion into corresponding self-sealing access slits in a sealing plug of a medical implant. Following the manufacture and assembly of the medical implant, including the mounting of the sealing structure or plug, and prior to the packaging of the medical implant, each protrusion of the insert is inserted into a corresponding self-sealing slit in the plug. The insert is then stored together with the medical implant in a storing package with the protrusions of the insert remaining within the corresponding self-sealing slits throughout the period of storing the medical implant prior to implantation. Thereby, the opposite surfaces of the self-sealing slit are kept apart, or at least the contact area between the surfaces is minimized, such that, the netting together of the slit is greatly reduced or eliminated.

The insert is preferably made from a flexible polymer material, such as polyethylene, polytetrafluoroethylene (Teflon®), polyethyleneterephtalate-G (PETG). However, other polymer materials are contemplated, provided that the chosen material has a flexibility that is sufficient for the protrusions not to damage the soft sealing plug when inserting the protrusions into the slit. Other materials, such as metals, can of course also be conceivable if the protrusion has a tip portion with a sufficiently blunt or rounded shape, such that the slit of the sealing plug will not be damaged.

The shape of the protrusions, or rather the end portion or tip of each protrusion, are formed such that insertion of the protrusion into the corresponding slit is facilitated, while the risk of damaging the slit during insertion is reduced. Therefore, the ideal tip shape depends on the chosen material. However, for a flexible plastic material, the tip of the protrusion is preferably formed in a cone, a double-bevel or a single-bevel configuration, which facilitates the insertion of the protrusions into the corresponding slits. Other configurations, such as a square or a rounded configuration, are also conceivable for reducing the risk of damaging the plug.

The insert is preferably formed from a thin strip that is cut out at one end for forming the protrusions. The insert can also be formed by molding.

Since the number of cardiac leads used can vary depending on the implant used for a particular patient, the number of connections in a terminal block, the number of fixing screws, and the number of access slits vary accordingly. Generally, the medical implant is connected to one or two leads, but three or four leads are also possible. Furthermore, each connection can be provided with one or more fixing screws, each fixing screw being accessed through a separate access slit. Therefore, the insert is provided with a chosen number of protrusions depending on the particular medical implant for which it is intended. Furthermore, the position(s) of the protrusion(s) is naturally adapted to the configuration and positioning of the access slit(s) on the medical implant.

According to one embodiment, the insert is preferably given a configuration at its proximal end that facilitates the removal of the insert from the medical implant, e.g. of the protrusion(s) from the corresponding access slit(s). Preferably, the proximal end of the insert is formed as a handle, or the like, that can be readily manipulated by the physician for removal of the insert from the medical implant prior to implantation of the implant.

When storing a medical implant, the implant is generally enclosed in a storing package having a lower portion or tray, and an upper portion or cover. According to an advantageous alternative embodiment, the insert, provided with the protrusions for insertion into the corresponding slits of the sealing plug, is connected to the bottom of the tray. Thus, upon removal of the implant from the storing package prior to implantation, the insert will be automatically withdrawn from the implant. Thus, the insert cannot interfere with any manipulation of the implant after removal of the implant from the storage package.

According to this embodiment, the insert is preferably made of the same material as the storage tray for falcilitating the adherence of the insert to the tray, e.g. by fusing the parts together. As an alternative, the insert can be formed integral with the storage tray, e.g. by molding.

Preferably, the insert has an elongated shape that is folded into the storage tray. Thus, the insert can be extended from the tray, as the bellows of an accordion, for providing the possibility of inserting the protrusions into the slits at a small distance away from the tray, thus facilitating the insertion. The insert is preferably folded in the storage tray such that the insert at its most proximal end is joined with the storage tray at a position directly underneath the access slit(s), when the implant is positioned in the tray. Thus, when the implant is pulled away from the tray, the action of pulling the insert out of the slits is facilitated and the risk of damaging the slits when removing the insert is considerably reduced.

As an alternative embodiment, the slits of the sealing plug can be produced with the aid of the protrusions of the insert, e.g. by molding the sealing plug about the protrusion.

With reference to FIGS. 1 and 2, there is shown a medical implant in the form of a pacemaker 1 when positioned on a storage tray 30. The pacemaker 1 comprises at one end a connector or header 2 containing a connector block 3 having a lumen or receptacle 4 for receiving the terminal pin of a cardiac lead (not shown). The opening of the receptacle 4 through which the terminal pin is inserted is sealed from the pacemaker surroundings, when the terminal pin is located within the receptacle 4, through a sealing structure (not shown) provided on the terminal pin and in the receptacle 4.

The connector block 3 is provided with a fixing screw 5 for securing the terminal pin in the receptacle 4 and for ensuring a stable electrical connection between the cardiac lead and the battery and circuitry of the pacemaker 1. The fixing screw 5 is preferably a socket screw having a socket 6 that can be accessed by a suitable tool through an opening provided in the header 2. For sealing the opening the header is provided with a flexible plug 20, which preferably is made of silicone rubber. For enabling access to the fixing screw 5, the plug 20 is provided with an access slit 21, as described in the U.S. patent above, through which a tool can be inserted for manipulation of the fixing screw 5. Due to radially directed compression forces exerted on the plug 20 by the surrounding walls of the opening in the header 2, the access slit 21 is self-sealing, whereby the plug 20 tightly seals the interior of the terminal block 3 from the pacemaker surroundings. The opposite surfaces of the access slit 21 sometimes is lubricated with a silicone-based lubricant for facilitating insertion of the tool through the access slit 21.

For illustrative purposes, FIGS. 1 and 2 show a pacemaker 1 with a single receptacle 4 for receiving a single cardiac lead that is secured by a single fixing screw 5. However, several cardiac leads can be connected to a single pacemaker. Furthermore, the terminal pin of each cardiac lead can be secured with more than one fixing screw. Therefore, the total number of access slits in a pacemaker can vary in accordance with the total number of fixing screws to be accessed.

When storing a pacemaker for a longer period of time, the access slit 21 of the plug 20 tends to net together, as mentioned above. According to the invention, an insert 10 is provided for insertion into the access slits 21 during storage, thereby preserving the function of the access slits 21 during extensive storage. The insert 10 preferably has a thin, elongated body portion 12 and is at its most distal end provided with protrusions 11, which are provided essentially perpendicular to the elongated body portion 12. The number of protrusions 11 correspond to the number of access slits 21 of the pacemaker 1, and the protrusions 11 are arranged in a configuration corresponding to the configuration of the access slits 21. The insert is preferably formed from a flexible plastic material in order for the protrusions not to damage the plugs 20 or the access slits 21 when inserting the protrusions 11 into the access slits 21. The tip portion of the protrusions 11 have an essentially rounded shape, but other alternative shapes are contemplated.

In FIG. 1, the insert 10 is shown as a separate element that is not attached to the storage tray 30. However, according to certain embodiments, the insert 10 can be connected to the tray 30, e.g. by forming an integral part thereof or being attached through an adhesive or by fusing. As is shown schematically in FIG. 1, for purposes that will be described below, the elongated body portion 12 of the insert 10 is preferably folded.

Figure 3B:
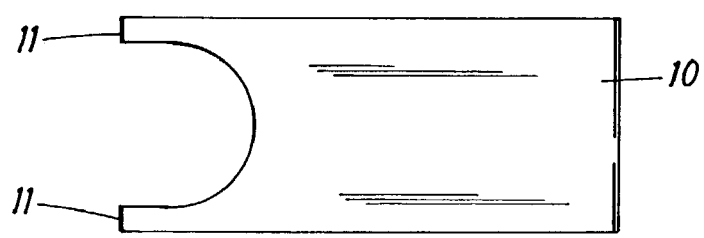

FIGS. 3a and 3b show side and top elevational views, respectively, of the insert 10 according to the invention shown in a folded configuration. The folds are provided at the proximal end of the insert 10 and of the elongated body portion 12 for enabling the insert 10 to fit into a storage tray 30 and for facilitating the removal of the insert 10 from the pacemaker 1. Furthermore, if connected to the storage tray 30, the insert 10 can be extended from the tray 30, for providing the possibility of inserting the protrusions 11 into the slits 21 at a small distance away from the tray 30, which facilitates the insertion. The preferred number of folds vary in accordance with the shape of the storage tray 30 and the method of manipulating the insert 10, i.e. if the insert 10 is integral with the tray 30 or if it is provided with a handle or the like.

Figure 4:
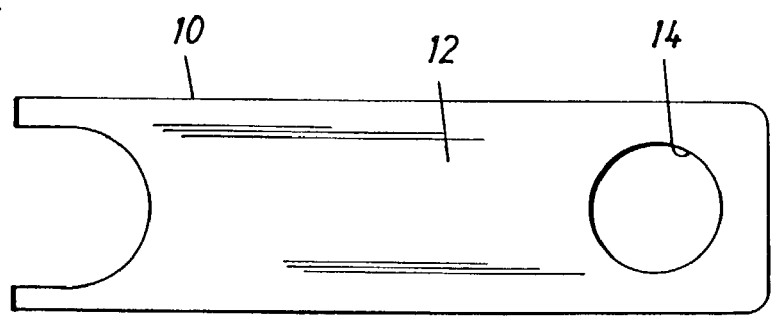
FIG. 4 is a top elevational view of the insert shown in FIGS. 3a and 3b, in an extended configuration.

FIG. 4 show an insert 10 according to an embodiment wherein the elongated body portion 12 is provided with a hole 14, which is arranged for facilitating the removal of the insert 10 front the pacemaker 1 by simply pulling the insert 10 out of the pacemaker 1. Thus, the elongated body portion 12 functions as a handle. The insert 10 according to the embodiment shown in FIG. 4 is preferably formed as a single element, which is not attached to the storage tray 30. Said insert 10 can be folded or be kept unfolded depending on the configuration of the storage tray.

Figure 5:
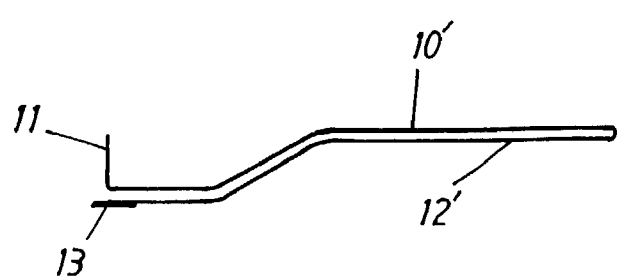
FIG. 5 is a side elevational view of an insert according to an alternative embodiment.

In FIG. 5 there is shown an alternative embodiment of an insert 10'. The insert 10' is provided with protrusions 11 in the same manner and with the same function as described above. The insert 10' is further provided with an elongated body portion 12', which is folded once such that the elongated body portion 12' is divided into an upper portion and a lower portion, which generally has the same extension in the longitudinal direction. Thereby, the elongated body portion 12' terminates at its proximal end at an area 13 located essentially straight underneath the protrusions 11 when the insert 10' is folded and the insert 10' and the pacemaker 1 are positioned for storing.

The insert 10' according to this embodiment is connected to a storage tray 30, either being integral with or attached to the storage tray 30. Thus, when removing the pacemaker 1 from the storage tray 30 prior to implantation of the pacemaker 1, the insert 10' will unfold and will obtain a generally linear extension in the longitudinal direction of the protrusions 11 and the access slits 21. Thus, the protrusions 11 are pulled out of the access slits 21 in a straight direction, thus eliminating turning of the protrusions 11 relative the access slits 21 during the removal of the insert 10'.

Although the present invention has been described by way of exemplifying embodiments with reference to the accompanying drawings, as is apparent to those skilled in the art various changes and modifications are possible without departing from the scope of the invention, which is defined in the accompanying claims.

The invention claimed is:

1. A sealing structure system for a medical implant, comprising:
   a storing package holding the medical implant; and
   said implant having at least one self-sealing access slit, said slit being provided with a removable insert for minimizing a contact area of opposite surfaces of the slit to prevent a sticking together of the opposite surfaces during storage of the medical implant in said storing package, said insert being removed during or after removal of the medical implant from the storing package and prior to access through said access slit.

2. The sealing structure according to claim 1 wherein said insert for minimizing the contact area is a removable insert, said insert being provided with at least one protrusion located in said slit.

3. The sealing structure according to claim 2 wherein said insert is attachable to said storing package which holds said medical implant.

4. The sealing structure according to claim 1 wherein the medical implant comprises a cardiac pacemaker.

5. The sealing structure according to claim 1 wherein the sealing structure is for plugging a hole having a fixing screw therein for fixing a cardiac lead received in a lead receiving aperture.

6. A connector system for a medical implant, comprising:
   a storing package for storing the connector system with the medical implant;
   a connector having an aperture for receiving a terminal of an electrical lead, said aperture being provided in a connector block mounted in the connector;
   a hole in the connector block having a fixing screw;
   a sealing structure positioned at one end of the connector block for closing off the hole having the fixing screw;
   said sealing structure having a self-sealing access slit self-sealing based on pressure exerted by a wall of the hole against the sealing structure; and
   a removable insert received within the self-sealing access slit for keeping walls of the access slit away from each other during storage of the medical implant in said storing package, said insert being removed during or after removal of the medical implant from the storing package and prior to access through said access slit.

7. A method for preserving a function during storage of at least one self-sealing access slit in a sealing structure mounted in a medical implant, said sealing structure being provided with at least one slit, comprising the steps of:
   retaining a protrusion comprising a removable insert within said at least one slit during storage in a storing package of the medical implant to preserve a function of said slit; and
   removing said protrusion from said slit prior to implantation of the medical implant to allow access of a tool through said slit.

8. The method according to claim 7 comprising the further steps of
   providing said storing package with said insert;
   storing the medical implant in said storing package; and
   removing the medical implant from said storing package prior to implantation, thus also removing the protrusion from the slit.

9. The method according to claim 7 wherein the sealing structure is received in a hole and wherein walls of the hole press against the sealing structure to self-seal the access slit.

10. The method according to claim 7 wherein the medical implant comprises a cardiac pacemaker and the sealing structure is provided to block off access to a fixing screw for retaining a cardiac lead.

11. A method for preserving a self-sealing access slit in a sealing structure of an electrical lead connector for a medical implant, comprising the steps of:
   providing a storing package for the medical implant;
   providing a self-sealing access slit in a sealing structure which self-seals based on pressure of a hole wall on the sealing structure;

for preserving an integrity of the self-sealing access slit during storage of the medical implant in said storing package, placing a removable insert into the access slit to substantially keep walls of the access slit away from each other during storage; and removing the insert during or after the removal of the implant from the storing package and prior to access through said access slit.

* * * * *